US006630545B2

(12) United States Patent
Arriola et al.

(10) Patent No.: US 6,630,545 B2
(45) Date of Patent: Oct. 7, 2003

(54) POLYMERIZATION PROCESS

(75) Inventors: Daniel J. Arriola, Midland, MI (US); Marilyn Bokota, Beaverton, MI (US); Francis J. Timmers, Midland, MI (US)

(73) Assignee: The Dow Chemical Company, Midland, MI (US)

( * ) Notice: Subject to any disclaimer, the term of this patent is extended or adjusted under 35 U.S.C. 154(b) by 33 days.

(21) Appl. No.: 09/954,551

(22) Filed: Sep. 17, 2001

(65) Prior Publication Data

US 2002/0037981 A1 Mar. 28, 2002

Related U.S. Application Data

(60) Continuation-in-part of application No. 09/598,803, filed on Jun. 21, 2000, now Pat. No. 6,323,294, which is a division of application No. 09/122,958, filed on Jul. 27, 1998, now Pat. No. 6,150,297.
(60) Provisional application No. 60/059,000, filed on Sep. 15, 1997.

(51) Int. Cl.[7] ............... C08F 4/76; C08F 212/08; B01J 31/38
(52) U.S. Cl. ............ 526/127; 526/160; 526/161; 526/347; 526/943; 502/152; 502/155
(58) Field of Search ................ 526/160, 943, 526/346, 347, 161, 127; 502/152, 155

(56) References Cited

U.S. PATENT DOCUMENTS

| 5,321,106 | A | | 6/1994 | LaPointe et al. |
|---|---|---|---|---|
| 5,374,696 | A | | 12/1994 | Rosen et al. |
| 5,436,304 | A | | 7/1995 | Griffin et al. |
| 5,470,993 | A | | 11/1995 | Devore et al. |
| 5,486,632 | A | | 1/1996 | Devore et al. |
| 5,541,270 | A | | 7/1996 | Chinh et al. |
| 5,541,349 | A | | 7/1996 | Wilson et al. |
| 5,543,480 | A | * | 8/1996 | Patton et al. ............... 526/126 |
| 5,703,187 | A | | 12/1997 | Timmers et al. |
| 5,721,185 | A | | 2/1998 | LaPointe et al. |

FOREIGN PATENT DOCUMENTS

| WO | WO97/15583 | 5/1997 |
|---|---|---|
| WO | WO97/19463 | 5/1997 |

OTHER PUBLICATIONS

Schneider et al., Journal of Organometallic Chemistry 545–546 (1997) 291–295.*
Schneider et al., Organometallics 1997, 16, 3413–3420.*

* cited by examiner

Primary Examiner—Robert D. Harlan

(57) ABSTRACT

An improved catalyst composition for addition polymerizations comprising: (A) a Group 4 metal complex the includes an anionic, polycyclic, fused ring ligand system containing at least 4 fused rings, and bonded to M by means of delocalized π-electrons, (B) a cocatalyst, and (C) a $C_{4-5}$ conjugated diene.

6 Claims, No Drawings

POLYMERIZATION PROCESS

CROSS-REFERENCE TO RELATED APPLICATIONS

This is a continuation-in-part of U.S. Ser. No. 09/598,803, filed Jun. 21, 2000, now U.S. Pat. No. 6,323,294 which is a divisional of U.S. Ser. No. 09/122,958 filed on Jul. 27, 1998, now U.S. Pat. No. 6,150,297, and which claims benefit of priority from United States provisional application, 60/059,000 filed on Sep. 15, 1997.

BACKGROUND OF THE INVENTION

This invention relates to an improved solution polymerization process. In particular, the invention relates to the use of an additive with certain metal complexes to achieve improved catalyst efficiencies in the solution polymerization of olefin monomers.

Constrained geometry metal complexes and methods for their preparation are disclosed in U.S. Pat. No. 5,703,187. This publication also teaches the preparation of certain novel copolymers of ethylene and a hindered vinyl monomer, including monovinyl aromatic monomers, having a pseudo-random incorporation of the hindered vinyl monomer therein. Additional teachings of constrained geometry catalysts may be found in U.S. Pat. Nos. 5,321,106; 5,721,185; 5,374,696, 5,470,993, 5,541,349, and 5,486,632, as well as WO97/15583, and WO97/19463. Such catalysts based on a cyclopentaphenanthreneyl ring system ligand are disclosed in U.S. Pat. No. 6,150,297. It is with respect to such metal complexes that the present improvement relates.

SUMMARY OF THE INVENTION

According to the present invention there is provided an improved process for the polymerization of addition polymerizable monomers, especially $C_{2-20}$ olefin monomers or mixtures thereof, comprising contacting an olefin monomer or mixture of olefin monomers under addition polymerization conditions with a catalyst composition comprising the reaction product or admixture of:

(A) a metal complex corresponding to the formula:
    $CpZMX_xL_1X'_{x'}$ (IA);
    where Cp is an anionic, polycyclic, fused ring ligand system containing at least 4 fused rings, and bonded to M by means of delocalized $\pi$-electrons;
    M is titanium, zirconium or hafnium in the +2, +3 or +4 formal oxidation state;
    Z is either a cyclic or noncyclic ligand group containing delocalized $\pi$-electrons, including a second polycyclic ring system group as herein previously disclosed for Cp, said Z being bonded to M by means of delocalized n-electrons and optionally covalently bonded to Cp through a divalent bridging group, or Z is a divalent moiety lacking in delocalized $\pi$-electrons that is covalently bonded to Cp and M, or such a moiety comprising one $\sigma$-bond by which it is bonded to Cp, and a neutral two electron pair able to form a coordinate-covalent bond to M;
    X is a monovalent anionic ligand group having up to 60 atoms other than hydrogen;
    L independently each occurrence is a neutral ligating compound having up to 20 atoms;
    X' is a divalent anionic ligand group having up to 60 atoms;
    x is 0, 1, 2, or 3;
    l is a number from 0 to 2, and
    x' is 0 or 1,
(B) a cocatalyst able to form an active polymerization catalyst species in combination with (A); and
(C) a conjugated diene having 4 or 5 carbons, preferably 1,3-butadiene, 1,3-pentadiene, or 3-methyl-1,3-butadiene, the molar ratio of (A):(B) being from 1:10,000 to 100:1 and the molar ratio of (C) to addition polymerizable compound being from 1:100,000 to 1:4.

The conjugated diene may be added to the reaction mixture separate from the above metal complex and cocatalyst such as by including the same in the monomer mixture added to the reactor, or it may be combined with one or both (A) and (B) prior to addition of the resulting catalyst mixture to the reactor. Surprisingly, the combination of component (C) with other metal complexes does not appear to result in improved catalyst performance. In addition, the use of other unsaturated substances in place of component (C) does not result in improved catalyst efficiency. Moreover, if too much of component (C) is used in relation to other polymerizable monomers, polymer properties are adversely affected. Desirably, the quantity of component (C) used is sufficient to provide a molar ratio of (C) to addition polymerizable compounds used in the process of from 1:1,000 to 1:10.

Use of the present process is especially efficient in production of olefin homopolymers, copolymers of two or more olefins, in particular, copolymers of ethylene and a vinylaromatic monomer, such as styrene, and interpolymers of three or more polymerizable monomers over a wide range of polymerization conditions, and especially at elevated temperatures. The process is especially suited for the formation of copolymers of ethylene and vinylaromatic monomers such as styrene (ES polymers) and copolymers of ethylene, propylene and styrene (EPS polymers).

The ES polymers generated using the present catalyst possess the previously noted valuable property that they are characterized by regular, homogeneous incorporation of vinylaromatic monomer into the polymer chain, compared to conventional ES polymers in which the vinylaromatic monomer tends to be incorporated in clusters of alternating comonomers. Such polymers possess lower peak melting points and glass transition temperatures (Tg) at comparable compositions, polymer molecular weights and molecular weight distributions compared to previously known ES polymers.

The catalyst compositions may also include a support material and be used in olefin polymerization processes in a slurry or in the gas phase. The catalyst components may be prepolymerized with one or more olefin monomers in situ in a polymerization reactor or in a separate process with intermediate recovery of the prepolymerized catalyst prior to the primary polymerization process, as well.

DETAILED DESCRIPTION

All reference to the Periodic Table of the Elements herein shall refer to the Periodic Table of the Elements, published and copyrighted by CRC Press, Inc., 1999. Also, any reference to a Group or Groups shall be to the Group or Groups as reflected in this Periodic Table of the Elements using the IUPAC system for numbering groups.

Preferred Cp groups herein include cyclopentaphenanthrene- or polycyclic azulene-based ring system ligands, optionally substituted with one or more substituents selected from hydrocarbyl, silyl, germyl, halide, hydrocarbyloxy, hydrocarbylsiloxy, hydrocarbylsilylamino, di(hydrocarbyl)amino, hydrocarbyleneamino, di(hydrocarbyl)phosphino, hydrocarbylenephosphino, hydrocarbylsulfido, halo-substituted hydrocarbyl, hydrocarbyloxy-substituted hydrocarbyl, silyl-substituted hydrocarbyl, hydrocarbylsiloxy-substituted hydrocarbyl, hydrocarbylsilylamino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylenephosphino-substituted hydrocarbyl, or hydrocarbylsulfido-substituted hydrocarbyl groups, said Cp having up to 40 atoms not counting hydrogen atoms, and optionally two or more of the foregoing substituents may together form a divalent derivative, and further optionally one or more carbons of the cyclopentaphenanthrene- or polycyclic azulene-based ring system may be replaced by a nitrogen or phosphorus atom. Such cyclopentaphenanthrene- or polycyclic azulene-based ring systems occur in several isomeric arrangements of the various rings, conventionally indicated by use of an italicized letter in the name. All of the known non-equivalent isomeric forms of cyclopentaphenanthrene (indicated as the a, b, c and l forms) are suitable for use herein. Preferred cyclopentaphenanthreneyl ring system ligand are those based on cyclopenta[c]phenanthreneyl or cyclopenta[l] phenanthreneyl groups. Preferred polycyclic azulene based ligands are dihydrodibenzoazulene derivatives.

In the foregoing metal complexes Z, if not a Cp group, preferably comprises boron, or a member of Group 14 of the Periodic Table of the Elements, and also nitrogen, phosphorus, sulfur or oxygen, and has up to 30 atoms, not counting hydrogen.

Preferred metal complexes for use according to the present invention are 1H-cyclopenta[l]-phenanthreneyl metal complexes corresponding to the formula:

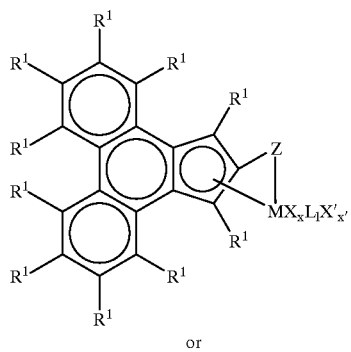

or

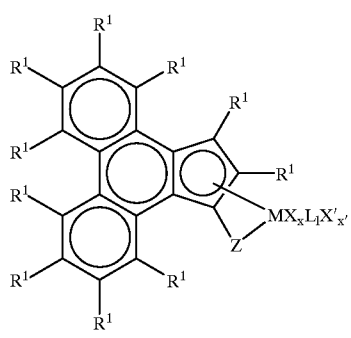

where M is titanium, zirconium or hafnium in the +2, +3 or +4 formal oxidation state;

$R^1$ independently each occurrence is hydrogen, hydrocarbyl, silyl, germyl, halide, hydrocarbyloxy, hydrocarbylsiloxy, hydrocarbylsilylamino, di(hydrocarbyl)amino, hydrocarbyleneamino, di(hydrocarbyl)phosphino, hydrocarbylene-phosphino, hydrocarbylsulfido, halo-substituted hydrocarbyl, hydrocarbyloxy-substituted hydrocarbyl, silyl-substituted hydrocarbyl, hydrocarbylsiloxy-substituted hydrocarbyl, hydrocarbylsilylamino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylenephosphino-substituted hydrocarbyl, or hydrocarbylsulfido-substituted hydrocarbyl, said $R^1$ group having up to 40 atoms not counting hydrogen atoms, and optionally two or more of the foregoing adjacent $R^1$ groups may together form a divalent derivative thereby forming a saturated or unsaturated fused ring, and further optionally one or more of the carbons of any of the rings may be replaced by a nitrogen or sulfur atom;

Z is a divalent moiety lacking in delocalized π-electrons, or such a moiety comprising one σ-bond and a neutral two electron pair able to form a coordinate-covalent bond to M, said Z comprising boron, or a member of Group 14 of the Periodic Table of the Elements, and also comprising nitrogen, phosphorus, sulfur or oxygen;

X is a monovalent anionic ligand group having up to 60 atoms exclusive of the class of ligands that are cyclic ligand groups bound to M through delocalized π-electrons;

L independently each occurrence is a neutral ligating compound having up to 20 atoms;

X' is a divalent anionic ligand group having up to 60 atoms;

x is 0, 1, 2, or 3;

l is a number from 0 to 2, and x' is 0 or 1.

Additional preferred metal complexes for use in the present invention are derivatives of dihydrodibenz[e,h] azulene or nitrogen containing analogues thereof corresponding to the following formulas:

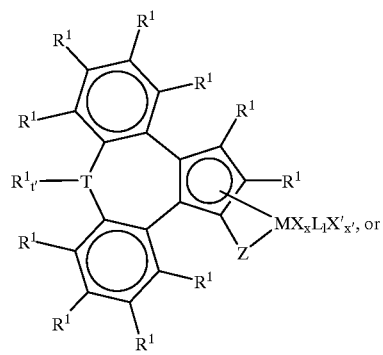

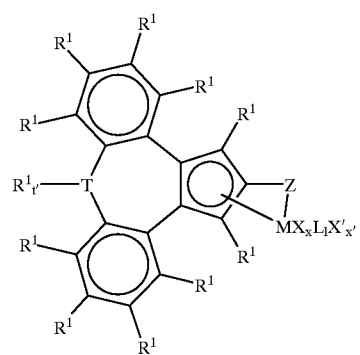

wherein,

T is carbon, or nitrogen;

when T is carbon, t' is 2, and when T is nitrogen, t' is 1;

M is titanium, zirconium or hafnium in the +2, +3 or +4 formal oxidation state;

$R^1$ independently each occurrence is hydrogen, hydrocarbyl, silyl, germyl, halide, hydrocarbyloxy, hydrocarbylsiloxy, hydrocarbylsilylamino, di(hydrocarbyl)amino, hydrocarbyleneamino, di(hydrocarbyl)phosphino, hydrocarbylene-phosphino, hydrocarbylsulfido, halo-substituted hydrocarbyl, hydrocarbyloxy-substituted hydrocarbyl, silyl-substituted hydrocarbyl, hydrocarbylsiloxy-substituted hydrocarbyl, hydrocarbylsilylamino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylenephosphino-substituted hydrocarbyl, or hydrocarbylsulfido-substituted hydrocarbyl, said $R^1$ group having up to 40 atoms not counting hydrogen atoms, and optionally two or more of the foregoing adjacent $R^1$ groups may together form a divalent derivative thereby forming a saturated or unsaturated fused ring, and further optionally one or more of the carbons of any of the rings may be replaced by a nitrogen or sulfur atom;

Z is a divalent moiety lacking in delocalized π-electrons, or such a moiety comprising one σ-bond and a neutral two electron pair able to form a coordinate-covalent bond to M, said Z comprising boron, or a member of Group 14 of the Periodic Table of the Elements, and also comprising nitrogen, phosphorus, sulfur or oxygen;

X is a monovalent anionic ligand group having up to 60 atoms exclusive of the class of ligands that are cyclic ligand groups bound to M through delocalized π-electrons;

L independently each occurrence is a neutral ligating compound having up to 20 atoms;

X' is a divalent anionic ligand group having up to 60 atoms;

x is 0, 1, 2, or 3;

l is a number from 0 to 2, and x' is 0 or 1.

In the foregoing metal complexes IB-IE, preferred L groups are carbon monoxide; phosphines, especially trimethylphosphine, triethylphosphine, triphenylphosphine and bis(1,2-dimethylphosphino)ethane; $P(OR^4)_3$, wherein $R^4$ is $C_{1-20}$ hydrocarbyl; ethers, especially tetrahydrofuran; amines, especially pyridine, bipyridine, tetramethylethylenediamine (TMEDA), and triethylamine; olefins; and neutral conjugated dienes having from 4 to 40, preferably 5 to 40 carbon atoms. Complexes including such neutral diene L groups are those wherein the metal is in the +2 formal oxidation state.

Further in reference to the metal complexes, X preferably is selected from the group consisting of hydro, halo, hydrocarbyl, silyl, and N,N-dialkylamino-substituted hydrocarbyl. The number of X groups depends on the oxidation state of M, whether Z is divalent or not and whether any neutral diene groups or divalent X' groups are present. The skilled artisan will appreciate that the quantity of the various substituents and the identity of Z are chosen to provide charge balance, thereby resulting in a neutral metal complex. For example, when Z is divalent, and x is zero, x' is two less than the formal oxidation state of M. When Z contains one neutral two electron coordinate-covalent bonding site, and M is in a formal oxidation state of +3, x may equal zero and x' equal 1, or x may equal 2 and x' equal zero. In a final example, if M is in a formal oxidation state of +2, Z may be a divalent ligand group, whereupon x and x' are both equal to zero and one neutral L ligand group may be present.

$R^1$ each occurrence preferably is hydrogen or a hydrocarbyl, hydrocarbyloxy, dihydrocarbylamino, hydrocarbyleneamino, dihydrocarbylamino-substituted hydrocarbyl group, or hydrocarbyleneamino-substituted hydrocarbyl group of up to 20 atoms not counting hydrogen, and optionally two $R^1$ groups may be joined together;

Z is —Y—Z'— wherein:

Y is —O—, —S—, —NR'$^5$—, —PR$^5$—; —NR$^5{}_2$, or —PR$^5{}_2$;

Z' is SiR$^6{}_2$, CR$^6{}_2$, SiR$^6{}_2$SiR$^6{}_2$, CR$^6{}_2$CR$^6{}_2$, CR$^6$=CR$^6$, CR$^6{}_2$SiR$^6{}_2$, BR$^6$, BR$^6$L", or GeR$^6{}_2$;

$R^5$ each occurrence is independently hydrocarbyl, trihydrocarbylsilyl, or trihydrocarbylsilylhydrocarbyl, said $R^5$ having up to 20 atoms other than hydrogen, and optionally two $R^5$ groups or $R^5$ together with Y form a ring system;

$R^6$ each occurrence is independently hydrogen, or a member selected from hydrocarbyl, hydrocarbyloxy, silyl, halogenated alkyl, halogenated aryl, —NR$^2{}_2$ and combinations thereof, said $R^6$ having up to 20 non-hydrogen atoms, and optionally, two $R^6$ groups form a ring system, most preferably Z is $Si(CH_3)_2$—$N(C(CH_3)_3$—;

Cyclopentaphenanthreneyl ligands are known ligands or may be readily prepared from known compounds by one skilled in the art, using published techniques or techniques analogous to published techniques. For example, 1H-cyclopenta[l]phenanthrene which corresponds to the formula:

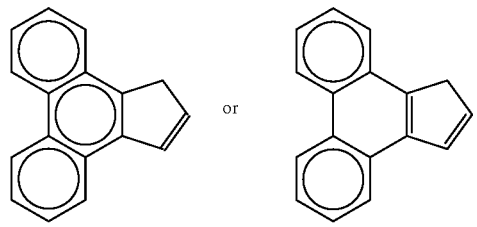

is a known compound. It, as well as the corresponding lithium salt, 1H-cyclopenta[l]-phenanthrene-2-yl, were disclosed in *J. Org. Chem.* (54), 171–175 (1989). Metal complexes thereof suitable for use herein are disclosed in U.S. Pat. No. 6,150,297.

Azuleneyl complexes and derivatives thereof suitable for use herein are similarly disclosed in U.S. Ser. No. 09/879, 463, filed Jun. 12, 2001, entitled, "Polycyclic, fused ring compounds, metal complexes and polymerization process".

More preferred cyclopentaphenanthrenyl ring system ligand metal complexes used according to the present invention are 1H-cyclopenta[l]phenanthrene-2-yl complexes corresponding to the formula:

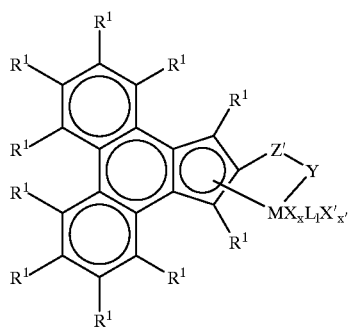

(IF)

wherein:
M is titanium;
R$^1$ each occurrence is hydrogen or a hydrocarbyl, amino or amino-substituted hydrocarbyl group of up to 20 atoms other than hydrogen;
Y is —O—, —S—, —NR$^5$—, —PR$^5$—; —NR$^5_2$, or —PR$^5_2$;
Z' is SiR$^5_2$, CR$^5_2$, SiR$^5_2$SiR$^5_2$, CR$_2$R$^5_2$, CR$^5$=CR$^5$, CR$^5_2$SiR$^5_2$, BR$^5$, or GeR$^5_2$;
R$^5$ each occurrence is independently hydrogen, or a member selected from hydrocarbyl, hydrocarbyloxy, silyl, halogenated alkyl, halogenated aryl, and combinations thereof, said R$^5$ having up to 20 non-hydrogen atoms, and optionally, two R$^5$ groups from Z' (when R$^5$ is not hydrogen), or an R$^5$ group from Z' and an R$^5$ group from Y form a ring system;
X, L, and X' are as previously defined;
x is 0, 1 or 2;
l is 0 or 1; and
x' is 0 or 1;
with the proviso that:
when x is 2, x' is zero, M is in the +4 formal oxidation state (or M is in the +3 formal oxidation state if Y is —NR$^5_2$ or —PR$^5_2$), and X is an anionic ligand selected from the group consisting of halide, hydrocarbyl, hydrocarbyloxy, di(hydrocarbyl)amido, di(hydrocarbyl)phosphido, hydrocarbylsulfido, and silyl groups, as well as halo-, di(hydrocarbyl)amino-, hydrocarbyloxy-, and di(hydrocarbyl)phosphino-substituted derivatives thereof, said X group having up to 30 atoms not counting hydrogen,
when x is 0 and x' is 1, M is in the +4 formal oxidation state, and X' is a dianionic ligand selected from the group consisting of hydrocarbadiyl, oxyhydrocarbylene, and hydrocarbylenedioxy groups, said X group having up to 30 nonhydrogen atoms,
when x is 1, and x' is 0, M is in the +3 formal oxidation state, and X is a stabilizing anionic ligand group selected from the group consisting of allyl, 2-(N,N-dimethylamino)phenyl, 2-(N,N-dimethylaminomethyl)phenyl, and 2-(N,N-dimethylamino)benzyl, and
when x and x' are both 0, l is 1, M is in the +2 formal oxidation state, and L is a neutral, conjugated or nonconjugated diene, optionally substituted with one or more hydrocarbyl groups, said L having up to 40 carbon atoms and being bound to M by means of delocalized π-electrons thereof.

Most preferred metal complexes are those according to the previous formula (ID), wherein M, R', X, L, X', Z', Y, x, l and x' are as previously defined, with the proviso that:

when x is 2, l and x' are both zero, M is in the +4 formal oxidation state, and X is independently each occurrence methyl, benzyl, or halide;
when x and are zero, x' is one, and M is in the +4 formal oxidation state, X' is a 1,4-butadienyl group that forms a metallocyclopentene ring with M,
when x is 1, l and x' are zero, M is in the +3 formal oxidation state, and X is 2-(N,N-dimethylamino)benzyl; and
when x and x' are 0, l is 1, M is in the +2 formal oxidation state, and L is 1,4-diphenyl-1,3-butadiene or 1,3-pentadiene.

Especially preferred coordination complexes corresponding to the previous formula (ID) are uniquely substituted depending on the particular end use thereof. In particular, highly useful metal complexes for use in catalyst compositions for the copolymerization of ethylene, one or more monovinyl aromatic monomers, and optionally an α-olefin, cyclic olefin or diolefin comprise the foregoing complexes (ID) wherein M is titanium, X is chloride or methyl, Z' is dimethylsilandiyl, Y is t-butylamido or phenylamido, x is 2, and l and x' are 0, or wherein M is titanium, X' is 1,3-pentadiene, Z' is dimethylsilandiyl, Y is t-butylamido or phenylamido, x and x' are 0 and l is 1.

Illustrative metal complexes that may be employed in the practice of the present invention include:
(t-butylamido)dimethyl(1H-cyclopenta[l]-phenanthrene-2-yl)silanetitanium (II) 1,4-diphenyl-1,3-butadiene,
(t-butylamido)dimethyl(1H-cyclopenta[l1]-phenanthrene-2-yl)silanetitanium(II) 1,3-pentadiene,
(t-butylamido)dimethyl(1H-cyclopenta[l]-phenanthrene-2-yl)silanetitanium(III) 2-(N,N-dimethylamino)benzyl,
(t-butylamido)dimethyl(1H-cyclopenta[l]-phenanthren-2-eyl)silanetitanium(IV) dichloride,
(t-butylamido)dimethyl(1H-cyclopenta[l]-phenanthrene-2-yl)silanetitanium(IV) dimethyl,
(t-butylamido)dimethyl(1H-cyclopenta[l]-phenanthrene-2-yl)silanetitanium(IV) dibenzyl,
(isopropylamido)dimethyl(1H-cyclopenta[l]-phenanthrene-2-yl)silanetitanium (II) 1,4-diphenyl-1,3-butadiene,
(isopropylamido)dimethyl(1H-cyclopenta[l1]-phenanthrene-2-yl)silanetitanium(II) 1,3-pentadiene,
(isopropylamido)dimethyl(1H-cyclopenta[l]-phenanthrene-2-yl)silanetitanium(III) 2-(N,N-dimethylamino)benzyl,
(isopropylamido)dimethyl(1H-cyclopenta[l]-phenanthrene-2-yl)silanetitanium(IV) dichloride,
(isopropylamido)dimethyl(1H-cyclopenta[l]-phenanthrene-2-yl)silanetitanium(IV) dimethyl,
(isopropylamido)dimethyl(1H-cyclopenta[l]-phenanthrene-2-yl)silanetitanium(IV) dibenzyl,
(benzylamido)dimethyl(1H-cyclopenta[l]-phenanthrene-2-yl)silanetitanium (II) 1,4-diphenyl-1,3-butadiene,
(benzylamido)dimethyl(1H-cyclopenta[l1]-phenanthrene-2-yl)silanetitanium(II) 1,3-pentadiene,
(benzylamido)dimethyl(1H-cyclopenta[l]-phenanthrene-2-yl)silanetitanium(III) 2-(N,N-dimethylamino)benzyl,
(benzylamido)dimethyl(1H-cyclopenta[l]-phenanthrene-2-yl)silanetitanium(IV) dichloride,
(benzylamido)dimethyl(1H-cyclopenta[l]-phenanthrene-2-yl)silanetitanium(M) dimethyl,
(benzylamido)dimethyl(1H-cyclopenta[l]-phenanthrene-2-yl)silanetitanium(IV) dibenzyl,
(cyclohexylamido)dimethyl(1H-cyclopenta[l]-phenanthrene-2-yl)silanetitanium (II) 1,4-diphenyl-1,3-butadiene,
(cyclohexylamido)dimethyl(1H-cyclopenta[l1]-phenanthrene-2-yl)silanetitanium(II) 1,3-pentadiene, (cyclohexylamido)dimethyl(1H-cyclopenta[l]-
phenanthrene-2-yl)silanetitanium(III) 2-(N,N-
dimethylamino)benzyl,
(cyclohexylamido)dimethyl(1H-cyclopenta[l]-
phenanthrene-2-yl)silanetitanium(IV) dichloride,
(cyclohexylamido)dimethyl(1H-cyclopenta[l]-
phenanthrene-2-yl)silanetitanium(IV) dimethyl,
(cyclohexylamido)dimethyl(1H-cyclopenta[l]-
phenanthrene-2-yl)silanetitanium(IV) dibenzyl,
cyclododecylamido)dimethyl(1H-cyclopenta[l]-
phenanthrene-2-yl)silanetitanium(II) 1,4-diphenyl-1,3-
butadiene,
(cyclododecylamido)dimethyl(1H-cyclopenta[l1]-
phenanthrene-2-yl)silanetitanium(II) 1,3-pentadiene,
(cyclododecylamido)dimethyl(1H-cyclopenta[l]-
phenanthrene-2-yl)silanetitanium(III) 2-(N,N-
dimethylamino)benzyl,
(cyclododecylamido)dimethyl(1H-cyclopenta[l]-
phenanthrene-2-yl)silanetitanium(IV) dichloride,
(cyclododecylamido)dimethyl(1H-cyclopenta[l]-
phenanthrene-2-yl)silanetitanium(IV) dimethyl,
(cyclododecylamido)dimethyl(1H-cyclopenta[l]-
phenanthrene-2-yl)silanetitanium(IV) dibenzyl,
(t-butylamido)dimethyl(1-methyl-1H-cyclopenta[l]-
phenanthrene-2-yl)silanetitanium (II) 1,4-diphenyl-1,3-
butadiene,
(t-butylamido)dimethyl(1-methyl-1H-cyclopenta[l1]-
phenanthrene-2-yl)silanetitanium(II) 1,3-pentadiene,
(t-butylamido)dimethyl(1-methyl-1H-cyclopenta[l]-
phenanthrene-2-yl)silanetitanium(III) 2-(N,N-
dimethylamino)benzyl,
(t-butylamido)dimethyl(1-methyl-1H-cyclopenta[l]-
phenanthrene-2-yl)silanetitanium(IV) dichloride,
(t-butylamido)dimethyl(1-methyl-1H-cyclopenta[l]-
phenanthrene-2-yl)silanetitanium(IV) dimethyl,
(t-butylamido)dimethyl(1-methyl-1H-cyclopenta[l]-
phenanthrene-2-yl)silanetitanium (IV) dibenzyl,
(isopropylamido)dimethyl(1-methyl-1H-cyclopenta[l]-
phenanthrene-2-yl)silanetitanium (II) 1,4-diphenyl-1,3-
butadiene,
(isopropylamido)dimethyl(1-methyl-1H-cyclopenta[l1]-
phenanthrene-2-yl)silanetitanium(II) 1,3-pentadiene,
(isopropylamido)dimethyl(1-methyl-1H-cyclopenta[l]-
phenanthrene-2-yl)silanetitanium(III) 2-(N,N-
dimethylamino)benzyl,
(isopropylamido)dimethyl(1-methyl-1H-cyclopenta[l]-
phenanthrene-2-yl)silanetitanium(IV) dichloride,
(isopropylamido)dimethyl(1-methyl-1H-cyclopenta[l]-
phenanthrene-2-yl)silanetitanium(IV) dimethyl,
(isopropylamido)dimethyl(1-methyl-1H-cyclopenta[l]-
phenanthrene-2-yl)silanetitanium(IV) dibenzyl,
(benzylamido)dimethyl(1-methyl-1H-cyclopenta[l]-
phenanthrene-2-yl)silanetitanium (II) 1,4-diphenyl-1,3-
butadiene,
(benzylamido)dimethyl(1-methyl-1H-cyclopenta[l1]-
phenanthrene-2-yl)silanetitanium(II) 1,3-pentadiene,
(benzylamido)dimethyl(1-methyl-1H-cyclopenta[l]-
phenanthrene-2-yl)silanetitanium(III) 2-(N,N-
dimethylamino)benzyl,
(benzylamido)dimethyl(1-methyl-1H-cyclopenta[l]-
phenanthrene-2-yl)silanetitanium(IV) dichloride,
(benzylamido)dimethyl(1-methyl-1H-cyclopenta[l]-
phenanthrene-2-yl)silanetitanium(IV) dimethyl,
(benzylamido)dimethyl(1-methyl-1H-cyclopenta[l]-
phenanthrene-2-yl)silanetitanium(IV) dibenzyl,
(cyclohexylamido)dimethyl(1-methyl-1H-cyclopenta[l]-
phenanthrene-2-yl)silanetitanium (II) 1,4-diphenyl-1,3-
butadiene,
(cyclohexylamido)dimethyl(1-methyl-1H-cyclopenta[l1]-
phenanthrene-2-yl)silanetitanium(II) 1,3-pentadiene,
(cyclohexylamido)dimethyl(1-methyl-1H-cyclopenta[l]-
phenanthrene-2-yl)silanetitanium(III) 2-(N,N-
dimethylamino)benzyl,
(cyclohexylamido)dimethyl(1-methyl-1H-cyclopenta[l]-
phenanthrene-2-yl)silanetitanium(IV) dichloride,
(cyclohexylamido)dimethyl(1-methyl-1H-cyclopenta[l]-
phenanthrene-2-yl)silanetitanium(IV) dimethyl,
(cyclohexylamido)dimethyl(1-methyl-1H-cyclopenta[l]-
phenanthrene-2-yl)silanetitanium(IV) dibenzyl,
cyclododecylamido)dimethyl(1-methyl-1H-cyclopenta[l]-
phenanthrene-2-yl)silanetitanium (II) 1,4-diphenyl-1,3-
butadiene,
(cyclododecylamido)dimethyl(1-methyl-1H-cyclopenta[l1]-
phenanthrene-2-yl)silanetitanium(II) 1,3-pentadiene,
(cyclododecylamido)dimethyl(1-methyl-1H-cyclopenta[l]-
phenanthrene-2-yl)silanetitanium(III) 2-(N,N-
dimethylamino)benzyl,
(cyclododecylamido)dimethyl(1-methyl-1H-cyclopenta[l]-
phenanthrene-2-yl)silanetitanium(IV) dichloride,
(cyclododecylamido)dimethyl(1-methyl-1H-cyclopenta[l]-
phenanthrene-2-yl)silanetitanium(IV) dimethyl,
(cyclododecylamido)dimethyl(1-methyl-1H-cyclopenta[l]-
phenanthrene-2-yl)silanetitanium(IV) dibenzyl,
(t-butylamido)dimethyl(1,3-dimethyl-1H-cyclopenta[l]-
phenanthrene-2-yl)silanetitanium (II) 1,4-diphenyl-1,3-
butadiene,
(t-butylamido)dimethyl(1,3-dimethyl-1H-cyclopenta[l1]-
phenanthrene-2-yl)silanetitanium(II) 1,3-pentadiene,
(t-butylamido)dimethyl(1,3-dimethyl-1H-cyclopenta[l]-
phenanthrene-2-yl)silanetitanium(III) 2-(N,N-
dimethylamino)benzyl,
(t-butylamido)dimethyl(1,3-dimethyl-1H-cyclopenta[l]-
phenanthrene-2-yl)silanetitanium(IV) dichloride,
(t-butylamido)dimethyl(1,3-dimethyl-1H-cyclopenta[l]-
phenanthrene-2-yl)silanetitanium(IV) dimethyl,
(t-butylamido)dimethyl(1,3-dimethyl-1H-cyclopenta[l]-
phenanthrene-2-yl)silanetitanium(IV) dibenzyl,
(isopropylamido)dimethyl(1,3-dimethyl-1H-cyclopenta[l]-
phenanthrene-2-yl)silanetitanium (II) 1,4-diphenyl-1,3-
butadiene,
(isopropylamido)dimethyl(1,3-dimethyl-1H-cyclopenta[l1]-
phenanthrene-2-yl)silanetitanium(II) 1,3-pentadiene,
(isopropylamido)dimethyl(1,3-dimethyl-1H-cyclopenta[l]-
phenanthrene-2-yl)silanetitanium(III) 2-(N,N-
dimethylamino)benzyl,
(isopropylamido)dimethyl(1,3-dimethyl-1H-cyclopenta[l]-
phenanthrene-2-yl)silanetitanium(IV) dichloride,
(isopropylamido)dimethyl(1,3-dimethyl-1H-cyclopenta[l]-
phenanthrene-2-yl)silanetitanium(IV) dimethyl,
(isopropylamido)dimethyl(1,3-dimethyl-1H-cyclopenta[l]-
phenanthrene-2-yl)silanetitanium(IV) dibenzyl,
(benzylamido)dimethyl(1,3-dimethyl-1H-cyclopenta[l]-
phenanthrene-2-yl)silanetitanium (II) 1,4-diphenyl-1,3-
butadiene,
(benzylamido)dimethyl(1,3-dimethyl-1H-cyclopenta[l1]-
phenanthrene-2-yl)silanetitanium(II) 1,3-pentadiene,
(benzylamido)dimethyl(1,3-dimethyl-1H-cyclopenta[l]-
phenanthrene-2-yl)silanetitanium(III) 2-(N,N-
dimethylamino)benzyl,
(benzylamido)dimethyl(1,3-dimethyl-1H-cyclopenta[l]-
phenanthrene-2-yl)silanetitanium(IV) dichloride,
(benzylamido)dimethyl(1,3-dimethyl-1H-cyclopenta[l]-
phenanthrene-2-yl)silanetitanium(IV) dimethyl,
(benzylamido)dimethyl(1,3-dimethyl-1H-cyclopenta[l]-
phenanthrene-2-yl)silanetitanium(IV) dibenzyl, (cyclohexylamido)dimethyl(1,3-dimethyl-1H-cyclopenta[l]-phenanthrene-2-yl)silanetitanium (II)1,4-diphenyl-1,3-butadiene,
(cyclohexylamido)dimethyl(1,3-dimethyl-1H-cyclopenta[l1]-phenanthrene-2-yl)silanetitanium(II) 1,3-pentadiene,
(cyclohexylamido)dimethyl(1,3-dimethyl-1H-cyclopenta[l]-phenanthrene-2-yl)silanetitanium(III) 2-(N,N-dimethylamino)benzyl,
(cyclohexylamido)dimethyl(1,3-dimethyl-1H-cyclopenta[l]-phenanthrene-2-yl)silanetitanium(IV) dichloride,
(cyclohexylamido)dimethyl(1,3-dimethyl-1H-cyclopenta[l]-phenanthrene-2-yl)silanetitanium(IV) dimethyl,
(cyclohexylamido)dimethyl(1,3-dimethyl-1H-cyclopenta[l]-phenanthrene-2-yl)silanetitanium(IV) dibenzyl,
cyclododecylamido)dimethyl(1,3-dimethyl-1H-cyclopenta[l]-phenanthrene-2-yl)silanetitanium(II) 1,4-diphenyl-1,3-butadiene,
(cyclododecylamido)dimethyl(1,3-dimethyl-1H-cyclopenta[l1]-phenanthrene-2-yl)silanetitanium(II) 1,3-pentadiene,
(cyclododecylamido)dimethyl(1,3-dimethyl-1H-cyclopenta[l]phenanthrene-2-yl)silanetitanium(III) 2-(N,N-dimethylamino)benzyl,
(cyclododecylamido)dimethyl(1,3-dimethyl-H-cyclopenta[l]-phenanthrene-2-yl)silanetitanium(IV) dichloride,
(cyclododecylamido)dimethyl(1,3-dimethyl-1H-cyclopenta[l]-phenanthrene-2-yl)silanetitanium(IV) dimethyl, and
(cyclododecylamido)dimethyl(1,3-dimethyl-1H-cyclopenta[l]-phenanthrene-2-yl)silanetitanium(IV) dibenzyl.

Suitable azulene derivatives for use herein include the following:
(2,8-dihydrodibenzo[e,h]azulene-2-yl)-N-(1,1-dimethylethyl)dimethyl-silanamide titanium (II) 1,4-diphenyl-1,3-butadiene,
(2,8-dihydrodibenzo[e,h]azulene-2-yl)-N-(1,1-dimethylethyl)dimethyl-silanamide titanium (II) 1,3-pentadiene,
((2,8-dihydrodibenzo[e,h]azulene-2-yl)-N-(1,1-dimethylethyl)dimethyl-silanamide titanium (III) 2-(N,N-dimethylamino)benzyl,
(2,8-dihydrodibenzo[e,h]azulene-2-yl)-N-(1,1-dimethylethyl)dimethyl-silanamide titanium (IV) dichloride,
2,8-dihydrodibenzo[e,h]azulene-2-yl)-N-(1,1-dimethylethyl)dimethyl-silanamide titanium (IV) dimethyl,
2,8-dihydrodibenzo[e,h]azulene-2-yl)-N-(1,1-dimethylethyl)dimethyl-silanamide titanium (IV) dibenzyl,
(2,8-dihydrodibenzo[e,h]azulene-2-yl)-N-(cyclohexyl)dimethyl-silanamide titanium (II) 1,4-diphenyl-1,3-butadiene,
(2,8-dihydrodibenzo[e,h]azulene-2-yl)-N-(cyclohexyl)dimethyl-silanamide titanium (II) 1,3-pentadiene,
((2,8-dihydrodibenzo[e,h]azulene-2-yl)-N-(cyclohexyl)dimethyl-silanamide titanium (III) 2-(N,N-dimethylamino)benzyl,
(2,8-dihydrodibenzo[e,h]azulene-2-yl)-N-(cyclohexyl)dimethyl-silanamide titanium (IV) dichloride,
2,8-dihydrodibenzo[e,h]azulene-2-yl)-N-(cyclohexyl)dimethyl-silanamide titanium (IV) dimethyl,
2,8-dihydrodibenzo[e,h]azulene-2-yl)-N-(cyclohexyl) dimethyl-silanamide titanium (IV) dibenzyl,
(2,8-dihydrodibenzo[e,h]azulene-1-yl)-N-(1,1-dimethylethyl)dimethyl-silanamide titanium (II) 1,4-diphenyl-1,3-butadiene,
(2,8-dihydrodibenzo[e,h]azulene-1-yl)-N-(1,1-dimethylethyl)dimethyl-silanamide titanium (II) 1,3-pentadiene,
((2,8-dihydrodibenzo[e,h]azulene-1-yl)-N-(1,1-dimethylethyl)dimethyl-silanamide titanium (III) 2-(N,N-dimethylamino)benzyl,
(2,8-dihydrodibenzo[e,h]azulene-1-yl)-N-(1,1-dimethylethyl)dimethyl-silanamide titanium (IV) dichloride,
2,8-dihydrodibenzo[e,h]azulene-1-yl)-N-(1,1-dimethylethyl)dimethyl-silanamide titanium (IV) dimethyl,
2,8-dihydrodibenzo[e,h]azulene-1-yl)-N-(1,1-dimethylethyl)dimethyl-silanamide titanium (IV) dibenzyl,
(2,8-dihydrodibenzo[e,h]azulene-1-yl)-N-(cyclohexyl)dimethyl-silanamide titanium (II) 1,4-diphenyl-1,3-butadiene,
(2,8-dihydrodibenzo[e,h]azulene-1-yl)-N-(cyclohexyl)dimethyl-silanamide titanium (II) 1,3-pentadiene,
((2,8-dihydrodibenzo[e,h]azulene-1-yl)-N-(cyclohexyl)dimethyl-silanamide titanium (III) 2-(N,N-dimethylamino)benzyl,
(2,8-dihydrodibenzo[e,h]azulene-1-yl)-N-(cyclohexyl)dimethyl-silanamide titanium (IV) dichloride,
2,8-dihydrodibenzo[e,h]azulene-1-yl)-N-(cyclohexyl)dimethylsilanamide titanium (IV) dimethyl,
2,8-dihydrodibenzo[e,h]azalene-1-yl)-N-(cyclohexyl)dimethylsilanamide titanium (IV) dibenzyl.

The complexes can be prepared by combining a Group 4 metal tetrahalide or tetraamide salt with the corresponding cyclopentaphenanthrenyl ring system ligand dianion in an inert diluent. Optionally a reducing agent can be employed to produce the lower oxidation state complexes, and standard ligand exchange procedures can by used to produce different ligand substituents. Processes that are suitably adapted for use herein are well known to synthetic organometallic chemists. The syntheses are preferably conducted in a suitable noninterfering solvent at a temperature from −100 to 300° C., preferably from −78 to 100° C., most preferably from 0 to 50° C. By the term "reducing agent" herein is meant a metal or compound which, under reducing conditions causes the metal M, to be reduced from a higher to a lower oxidation state. Examples of suitable metal reducing agents are alkali metals, alkaline earth metals, aluminum and zinc, alloys of alkali metals or alkaline earth metals such as sodium/mercury amalgam and sodium/potassium alloy. Examples of suitable reducing agent compounds are sodium naphthalenide, potassium graphite, lithium alkyls, lithium or potassium alkadienyls; and Grignard reagents. Most preferred reducing agents are the alkali metals or alkaline earth metals, especially lithium and magnesium metal.

Suitable reaction media for the formation of the complexes include aliphatic and aromatic hydrocarbons, ethers, and cyclic ethers, particularly branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; aromatic and hydrocarbyl-substituted aromatic compounds such as benzene, toluene, and xylene, $C_{1-4}$ dialkyl ethers, $C_{1-4}$ dialkyl ether derivatives of (poly)alkylene glycols, and tetrahydrofuran. Mixtures of the foregoing are also suitable.

The complexes are rendered catalytically active by combination with an activating cocatalyst (B). Suitable activating cocatalysts for use herein include polymeric or oligomeric alumoxanes, especially methylalumoxane (MAO), triisobutyl aluminum modified methylalumoxane (AO), or isobutylalumoxane; neutral Lewis acids, such as $C_{1-30}$ hydrocarbyl substituted Group 13 compounds, especially tri(hydrocarbyl)aluminum- or tri(hydrocarbyl)boron compounds and halogenated (including perhalogenated) derivatives thereof, having from 1 to 10 carbons in each hydrocarbyl or halogenated hydrocarbyl group, more especially perfluorinated tri(aryl)boron compounds, and most especially tris(pentafluorophenyl)borane; nonpolymeric, compatible, noncoordinating, ion forming compounds (including the use of such compounds under oxidizing conditions), especially the use of ammonium-, phosphonium-, oxonium-, carbonium-, silylium- or sulfonium- salts of compatible, noncoordinating anions, or ferrocenium salts of compatible, noncoordinating anions; and combinations of the foregoing activating cocatalysts. The foregoing activating cocatalysts have been previously taught with respect to different metal complexes in the following references: U.S. Pat. No. 5,153,157, U.S. Pat. No. 5,064,802, U.S. Pat. No. 5,321,106, U.S. Pat. No. 5,350,723, and U.S. Pat. No. 5,721,185.

Combinations of neutral Lewis acids, especially the combination of a trialkyl aluminum compound having from 1 to 4 carbons in each alkyl group and a halogenated tri (hydrocarbyl)boron compound having from 1 to 20 carbons in each hydrocarbyl group, especially trispentafluorophenyl) borane, further combinations of such neutral Lewis acid mixtures with a polymeric or oligomeric alumoxane, and combinations of a single neutral Lewis acid, especially tris(pentafluorophenyl)borane with a polymeric or oligomeric alumoxane are especially desirable activating cocatalysts. Preferred molar ratios of Group 4 metal complex:tris (pentafluorophenyl-borane:alumoxane are from 1:1:1 to 1:5:20, more preferably from 1:1:1.5 to 1:5:10.

Suitable ion forming compounds useful as cocatalysts in one embodiment of the present invention comprise a cation which is a Bronsted acid capable of donating a proton, and a compatible, noncoordinating anion, A. As used herein, the term "noncoordinating" means an anion or substance which either does not coordinate to the Group 4 metal containing precursor complex and the catalytic derivative derived therefrom, or which is only weakly coordinated to such complexes thereby remaining sufficiently labile to be displaced by a neutral Lewis base. A noncoordinating anion specifically refers to an anion which when functioning as a charge balancing anion in a cationic metal complex does not transfer an anionic substituent or fragment thereof to said cation thereby forming neutral complexes. "Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitrites. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

Preferably such cocatalysts may be represented by the following general formula:

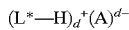

wherein:
L* is a neutral Lewis base;
(L*–H)+ is a conjugate Bronsted acid of L*;
$A^{d-}$ is a noncoordinating, compatible anion having a charge of d–, and
d is an integer from 1 to 3.

More preferably $A^{d-}$ corresponds to the formula: $[M'Q_4]^-$; wherein:
M' is boron or aluminum in the +3 formal oxidation state; and
Q independently each occurrence is selected from hydride, dialkylamido, halide, hydrocarbyl, hydrocarbyloxide, halosubstituted-hydrocarbyl, halosubstituted hydrocarbyloxy, and halo-substituted silylhydrocarbyl radicals (including perhalogenated hydrocarbyl-perhalogenated hydrocarbyloxy- and perhalogenated silylhydrocarbyl radicals), said Q having up to 20 carbons with the proviso that in not more than one occurrence is Q halide. Examples of suitable hydrocarbyloxide Q groups are disclosed in U.S. Pat. No. 5,296,433.

In a more preferred embodiment, d is one, that is, the counter ion has a single negative charge and is $A^-$. Activating cocatalysts comprising boron which are particularly useful in the preparation of catalysts of this invention may be represented by the following general formula:

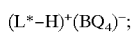

wherein:
L* is as previously defined;
B is boron in a formal oxidation state of 3; and
Q is a hydrocarbyl-, hydrocarbyloxy-, fluorinated hydrocarbyl-, fluorinated hydrocarbyloxy-, or fluorinated silylhydrocarbyl-group of up to 20 nonhydrogen atoms, with the proviso that in not more than one occasion is Q hydrocarbyl.

Preferred Lewis base salts are ammonium salts, more preferably trialkylammonium salts containing one or more $C_{12-40}$ alkyl groups. Most preferably, Q is each occurrence a fluorinated aryl group, especially, a pentafluorophenyl group.

Illustrative, but not limiting, examples of boron compounds which may be used as an activating cocatalyst in the preparation of the improved catalysts of this invention are tri-substituted ammonium salts such as:
trimethylammonium tetrakis(pentafluorophenyl) borate,
triethylammonium tetrakis(pentafluorophenyl) borate,
tripropylammonium tetrakis(pentafluorophenyl) borate,
tri(n-butyl)ammonium tetrakis(pentafluorophenyl) borate,
tri(sec-butyl)ammonium tetrakis(pentafluorophenyl) borate,
N,N-dimethylanilinium tetrakis(pentafluorophenyl) borate,
N,N-dimethylanilinium n-butyltris(pentafluorophenyl) borate,
N,N-dimethylanilinium benzyltris(pentafluorophenyl) borate,
N,N-dimethylanilinium tetrakis(4-(t-butyldimethylsilyl)-2, 3,5,6-tetrafluorophenyl) borate,
N,N-dimethylanilinium tetrakis(4-(triisopropylsilyl)-2,3,5, 6-tetrafluorophenyl) borate,
N,N-dimethylanilinium pentafluorophenoxytris (pentafluorophenyl) borate, N,N-diethylanilinium tetrakis(pentafluorophenyl) borate,
N,N-dimethyl-2,4,6-trimethylanilinium tetrakis(pentafluorophenyl) borate,
dimethyloctadecylammonium tetrakis(pentafluorophenyl) borate,
methyldioctadecylammonium tetrakis(pentafluorophenyl) borate,
dialkyl ammonium salts such as:
di-(i-propyl)ammonium tetrakis(pentafluorophenyl) borate,
methyloctadecylammonium tetrakis(pentafluorophenyl) borate,
methyloctadodecylammonium tetrakis(pentafluorophenyl) borate, and
dioctadecylammonium tetrakis(pentafluorophenyl) borate;
tri-substituted phosphonium salts such as:
triphenylphosphonium tetrakis(pentafluorophenyl) borate,
methyldioctadecylphosphonium tetrakis(pentafluorophenyl) borate, and
tri(2,6-dimethylphenyl)phosphonium tetrakis(pentafluorophenyl) borate;
di-substituted oxonium salts such as:
diphenyloxonium tetrakis(pentafluorophenyl) borate,
di(o-tolyl)oxonium tetrakis(pentafluorophenyl) borate, and
di(octadecyl)oxonium tetrakis(pentafluorophenyl) borate;
di-substituted sulfonium salts such as:
di(o-tolyl)sulfonium tetrakis(pentafluorophenyl) borate, and
methylcotadecylsulfonium tetrakis(pentafluorophenyl) borate.

Preferred (L*–H)$^+$ cations are methyldioctadecylammonium and dimethyloctadecylammonium.

Another suitable ion forming, activating cocatalyst comprises a salt of a cationic oxidizing agent and a noncoordinating, compatible anion represented by the formula:

$$(OX^{e+})_d(A^{d-})_e.$$

wherein:
Ox$^{e+}$ is a cationic oxidizing agent having a charge of e+;
e is an integer from 1 to 3; and
A$^{d-}$ and d are as previously defined.

Examples of cationic oxidizing agents include: ferrocenium, hydrocarbyl-substituted ferrocenium, Ag$^+$ or Pb$^{+2}$. Preferred embodiments of A$^{d-}$ are those anions previously defined with respect to the Bronsted acid containing activating cocatalysts, especially tetrakis(pentafluorophenyl)borate.

Another suitable ion forming, activating cocatalyst comprises a compound which is a salt of a carbenium ion and a noncoordinating, compatible anion represented by the formula:

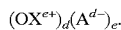$^+$A$^-$ wherein:
$^+$ is a C$_{1-20}$ carbenium ion; and
A$^-$ is as previously defined. A preferred carbenium ion is the trityl cation, that is triphenylmethylium.

A further suitable ion forming, activating cocatalyst comprises a compound which is a salt of a silylium ion and a noncoordinating, compatible anion represented by the formula:

$$(R^6{}_3Si)^+A^-$$

wherein:
R$^6$ is C$_{1-10}$ hydrocarbyl, and A is as previously defined.

Preferred silylium salt activating cocatalysts are trimethylsilylium tetrakispentafluorophenylborate, triethylsilylium tetrakispentafluorophenylborate and ether substituted adducts thereof. Silylium salts have been previously generically disclosed in J. Chem Soc. Chem. Comm., 1993, 383–384, as well as Lambert, J. B., et al., Organometallics, 1994, 13, 2430–2443. The use of the above silylium salts as activating cocatalysts for addition polymerization catalysts is disclosed in U.S. Pat. No. 5,625,087.

Certain complexes of alcohols, mercaptans, silanols, and oximes with tris(pentafluorophenyl)borane are also effective catalyst activators and may be used according to the present invention. Such cocatalysts are disclosed in U.S. Pat. No. 5,296,433.

The molar ratio of catalyst/cocatalyst employed preferably ranges from 1:10,000 to 100:1, more preferably from 1:5000 to 10:1, most preferably from 1:1000 to 1:1. Alumoxane, when used by itself as an activating cocatalyst, is employed in large quantity, generally at least 100 times the quantity of metal complex on a molar basis. Tris(pentafluorophenyl)-borane, where used as an activating cocatalyst is employed in a molar ratio to the metal complex of form 0.5:1 to 10:1, more preferably from 1:1 to 6:1 most preferably from 1:1 to 5:1. The remaining activating cocatalysts are generally employed in approximately equimolar quantity with the metal complex.

The catalyst compositions, whether or not supported, may be used to polymerize ethylenically and/or acetylenically unsaturated monomers having from 2 to 100,000 carbon atoms either alone or in combination. The monomers for use herein include aliphatic and aromatic compounds containing vinylic unsaturation, as well as cyclic unsaturated compounds such as cyclobutene, cyclopentene, and norbornene, including norbornene substituted in the 5 and 6 position with C$_{1-20}$ hydrocarbyl groups, and C$_{6-40}$ diolefins. Also included are mixtures of such monomers, especially mixtures of C$_{2-8}$ olefins with C$_{6-40}$ diolefin compounds. Examples of suitable C$_{6-40}$ diolefin compounds include ethylidenenorbornene, 1,4-hexadiene, and norbornadiene. Long chain vinyl terminated monomers may be formed during the polymerization process, for example by the phenomenon of β-hydride elimination of a proton from a growing polymer chain. This process results in incorporation of such extremely long chains of preformed polymer into the resulting polymer, that is long chain branching.

Vinylaromatic monomers for use herein include C$_{8-20}$ aryl substituted ethylene compounds having the formula:

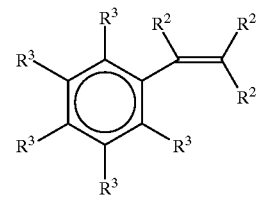

wherein:
R$^2$ independently each occurrence is hydrogen or C$_{1-4}$ alkyl, and
R$^3$ independently each occurrence is R$^2$ or halo.

Preferred monomers include the C$_{2-20}$ olefins especially ethylene, propylene, isobutylene, 1-butene, 1-pentene, 1-hexene, 3-methyl-i-pentene, 4-methyl-i-pentene, 1-octene, 1-decene, long chain macromolecular α-olefins, and mixtures thereof. Other preferred monomers include styrene, C$_{1-4}$ alkyl substituted styrene, tetrafluoroethylene, norbornene, vinylbenzocyclobutane, ethylidenenorbornene, 1,4-hexadiene, 1,7-octadiene, vinylcyclohexane, 4-vinylcyclohexene, divinylbenzene, and mixtures thereof with ethylene.

More preferred monomers include a combination of ethylene and one or more comonomers selected from monovinyl aromatic monomers, 4-vinylcyclohexene, vinylcyclohexane, norbornadiene, ethylidene-norbornene, $C_{3-10}$ aliphatic α-olefins (especially propylene, isobutylene, 1-butene, 1-hexene, 3-methyl-1-pentene, 4-methyl-1-pentene, and 1-octene), and $C_{6-40}$ dienes. Most preferred monomers are mixtures of ethylene and styrene; mixtures of ethylene, propylene and styrene; mixtures of ethylene, styrene and a nonconjugated diene, especially ethylidenenorbornene or 1,4-hexadiene, and mixtures of ethylene, propylene and a $C_{6-40}$ nonconjugated diene, especially ethylidenenorbornene or 1,4-hexadiene.

In general, the polymerization may be accomplished at conditions well known in the prior art for Ziegler-Natta or Kaminsky-Sinn type polymerization reactions, that is, temperatures from 0–250° C., preferably 30 to 200° C. and pressures from atmospheric to 10,000 atmospheres. Suspension, solution, slurry, gas phase, solid state powder polymerization or other process condition may be employed if desired. A support, especially silica, alumina, or a polymer (especially poly(tetrafluoroethylene) or a polyolefin) may be employed, and desirably is employed when the catalysts are used in a gas phase polymerization process. The support is preferably employed in an amount to provide a weight ratio of catalyst (based on metal):support from 1:100,000 to 1:10, more preferably from 1:50,000 to 1:20, and most preferably from 1:10,000 to 1:30.

In most polymerization reactions the molar ratio of catalyst:polymerizable compounds employed is from $10^{-12}$:1 to $10^{-1}$:1, more preferably from $10^{-9}$:1 to $10^{-5}$:1.

Suitable solvents use for solution polymerization are inert liquids. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and alkyl-substituted aromatic compounds such as benzene, toluene, xylene, and ethylbenzene. Suitable solvents also include liquid olefins which may act as monomers or comonomers.

The catalysts may be utilized in combination with at least one additional homogeneous or heterogeneous polymerization catalyst in the same reactor or in separate reactors connected in series or in parallel to prepare polymer blends having desirable properties. An example of such a process is disclosed in WO 94/00500, equivalent to U.S. Ser. No. 07/904,770, as well as U.S. Ser. No. 08/10958, filed Jan. 29, 1993.

Utilizing the present catalyst compositions, interpolymers of ethylene, one or more vinylaromatic monomers and optionally an α-olefin or a diolefin having densities from 0.85 g/cm³ to 1.1 g/cm³, melt flow rates from 0.01 to 20.0 dg/min, and incorporating large amounts of vinylaromatic monomer in a pseudo-random manner are readily attained in a highly efficient process. Pseudo-random incorporation of vinylaromatic monomers is a well known phenomena in which the monomer is essentially randomly incorporated into the polymer, excepting that two such vinylaromatic monomers having the same orientation may not succeed one another in the polymer chain. The procedure has been previously disclosed in U.S. Pat. No. 5,703,187.

The catalyst compositions of the present invention are also particularly advantageous for the production of ethylene homopolymers, ethylene/α-olefin copolymers, and interpolymers of ethylene a diene and optionally a $C_{3-20}$ α-olefin having high levels of long chain branching and comonomer incorporation. The use of the catalysts of the present invention in continuous polymerization processes, especially continuous, solution polymerization processes, allows for elevated reactor temperatures which favor the formation of vinyl terminated polymer chains that may be incorporated into a growing polymer, thereby giving a long chain branch. The use of the present catalyst compositions advantageously allows for the economical production of ethylene/α-olefin copolymers having processability similar to high pressure, free radical produced low density polyethylene.

The present catalyst compositions may be advantageously employed to prepare olefin polymers having improved processing properties by polymerizing ethylene alone or ethylene/α-olefin mixtures with low levels of a "H" branch inducing $C_{6-40}$ diene, such as norbornadiene, 1,7-octadiene, or 1,9-decadiene. The unique combination of elevated reactor temperatures, high molecular weight (or low melt indices) at high reactor temperatures and high comonomer reactivity advantageously allows for the economical production of polymers having excellent physical properties and processability. Preferably such polymers comprise ethylene, a $C_{3-20}$ α-olefin and a "H"-branching comonomer. Preferably, such polymers are produced in a solution process, most preferably a continuous solution process.

The catalyst composition may be prepared as a homogeneous catalyst by addition of the requisite components to a solvent in which polymerization will be carried out by solution polymerization procedures. The catalyst composition may also be prepared and employed as a heterogeneous catalyst by adsorbing the requisite components on an inert inorganic or organic particulated solid. Examples of such solids include, silica, silica gel, alumina, trialkylaluminum compounds, and organic or inorganic polymeric materials, especially polyolefins. In an preferred embodiment, a heterogeneous catalyst is prepared by co-precipitating the metal complex, an inert, inorganic compound and an activator, especially an ammonium salt of a hydroxyaryl (trispentafluorophenyl)borate, such as an ammonium salt of (4-hydroxy-3,5-ditertiarybutylphenyl) (trispentafluorophenylborate. A preferred inert, inorganic compound for use in this embodiment is a tri ($C_{1-4}$ alkyl) aluminum compound.

When prepared in heterogeneous or supported form, the catalyst composition is employed in a slurry or gas phase polymerization. As a practical limitation, slurry polymerization takes place in liquid diluents in which the polymer product is substantially insoluble. Preferably, the diluent for slurry polymerization is one or more hydrocarbons with less than 5 carbon atoms. If desired, saturated hydrocarbons such as ethane, propane or butane may be used in whole or part as the diluent. Likewise the α-olefin monomer or a mixture of different α-olefin monomers may be used in whole or part as the diluent. Most preferably at least a major part of the diluent comprises the α-olefin monomer or monomers to be polymerized.

At all times, the individual ingredients as well as the recovered catalyst components must be protected from oxygen and moisture. Therefore, the catalyst components and catalysts must be prepared and recovered in an oxygen and moisture free atmosphere. Preferably, therefore, the reactions are performed in the presence of an dry, inert gas such as, for example, nitrogen.

The polymerization may be carried out as a batchwise or a continuous polymerization process. A continuous process is preferred, in which event catalyst, ethylene, comonomer, and optionally solvent are continuously supplied to the reaction zone and polymer product continuously removed therefrom.

Without limiting in any way the scope of the invention, one means for carrying out such a polymerization process is as follows. In a stirred-tank reactor, the monomers to be polymerized are introduced continuously together with solvent and an optional chain transfer agent. The reactor contains a liquid phase composed substantially of monomers together with any solvent or additional diluent and dissolved polymer. If desired, a small amount of a "H"-branch inducing diene such as norbornadiene, 1,7-octadiene or 1,9-decadiene may also be added.

Catalyst (A), cocatalyst (B), and conjugated diene (C) are continuously introduced in the reactor liquid phase. The reactor temperature and pressure may be controlled by adjusting the solvent/monomer ratio, the catalyst addition rate, as well as by cooling or heating coils, jackets or both. The polymerization rate is controlled by the rate of catalyst addition. The ethylene content of the polymer product is determined by the ratio of ethylene to comonomer in the reactor, which is controlled by manipulating the respective feed rates of these components to the reactor. The polymer product molecular weight is controlled, optionally, by controlling other polymerization variables such as the temperature, monomer concentration, or by the previously mentioned chain transfer agent, such as a stream of hydrogen introduced to the reactor, as is well known in the art. The reactor effluent is contacted with a catalyst kill agent such as water. The polymer solution is optionally heated, and the polymer product is recovered by flashing off gaseous monomers as well as residual solvent or diluent at reduced pressure, and, if necessary, conducting further devolatilization in equipment such as a devolatilizing extruder. In a continuous process the mean residence time of the catalyst and polymer in the reactor generally is from 5 minutes to 8 hours, and preferably from 10 minutes to 6 hours. By using a catalyst that incorporates large amounts of hindered monovinyl monomer, such as a vinylaromatic monomer, hindered monovinyl homopolymer formed from residual quantities of the monomer are substantially reduced.

As previously mentioned, the catalyst compositions of the invention are capable of producing ES polymer having highly uniform vinylaromatic monomer incorporation. Such uniform ES polymers are characterized by a unique $^{13}C$ NMR signature. In particular, such polymers are characterized by a cluster index, $CI_{ES}$, which relates a ratio of two peaks in the $^{13}C$ NMR spectrum, $NMR_F/NMR_E$, wherein $NMR_F$ is the integrated area of the peak associated only with vinylaromatic monomer/ethylene/vinylaromatic monomer (SES) triads (commonly appearing at approximately 25 to 26.9 ppm) and $NMR_E$ is the integrated area of the peak associated only with triads containing a single incorporated vinylaromatic monomer (commonly appearing at approximately 27 to 29 ppm). It should be emphasized that in both types of polymers the vinylaromatic monomer is incorporated in a pseudo random manner, that is, successive or adjacent head to tail insertion of a vinyl aromatic monomer in the polymer chain is still prohibited. Such pseudo random nature characteristically produces a $^1H$ NMR spectrum of the polymer which lacks any appreciable peaks between the two peaks located at approximately 37 and 46 ppm respectively. However, in uniform ES polymers, lack of clustering of the incorporated vinylaromatic monomer into alternating monomer sequences can be identified by comparing the area of the $NMR_E$ peaks relative to $NMR_F$ peaks as a function of monomer composition in the polymer.

This cluster index, $CI_{ES}$, can be expressed mathematically through use of the following formula:

$$CI_{ES} = \left[\frac{NMR_F}{NMR_E}\right]\left[\frac{(4F_1 - 2)}{(1 - F_1)}\right]$$

where $F_1$ is the mole fraction of ethylene in the polymer. The uniform pseudo-random ES polymers of the invention are characterized by $CI_{ES}$ values less than 1.0 at polymer compositions of less than 50 mole percent polymerized vinylaromatic monomer, preferably $CI_{ES}$ values less than 0.95 at compositions of less than 47 mole percent polymerized vinylaromatic monomer.

EXAMPLES

The skilled artisan will appreciate that the invention disclosed herein may be practiced in the absence of any component which has not been specifically disclosed. The following examples are provided as further illustration of the invention and are not to be construed as limiting. Unless stated to the contrary all parts and percentages are expressed on a weight basis. All syntheses were performed under dry nitrogen atmosphere using a combination of glove box and high vacuum techniques. The term "overnight" refers to a period of time from 14 to 20 hours. The term "room temperature" refers to a temperature from 20 to 25° C.

Example 1

Ethylene or a combination of ethylene and styrene were polymerized in the following manner. A two-liter Parr reactor was charged with appropriate amounts of solvent (Isopar-E™ mixed alkanes solvent available from Exxon Chemicals Inc. (IPE) or toluene (TOL)) and optionally styrene comonomer. Comonomer 1,3-butadiene (BLD), illustrating the invention) or propylene (PR, comparative) was added in the desired amount, if used. Hydrogen was added (Δ10 psi, Δ70 kPa) as a molecular weight control agent by differential pressure expansion from a 75 mL addition tank at 275 psig (1.9 MPa). The reactor was heated to the desired reaction temperature and saturated with ethylene at the desired pressure. The appropriate amount of catalyst and cocatalyst (runs 1–15—trispentafluorophenylborane, runs 16 and 17—a 1:10 molar ratio mixture of armenium tetrakis (pentafluorophenyl)borate and MMAO) as 0.005M solutions in toluene were premixed in a glovebox to give a 1:3 molar ratio of catalyst and cocatalyst based on boron (runs 1–13) or a 1:1 molar ratio of catalyst and cocatalyst based on boron (runs 14–17), and transferred to a catalyst addition tank and injected into the reactor. The polymerization conditions were maintained for the desired time. Some reactions called for continuous supply of ethylene (identified in Table 1 by MPa), while others used only an initial charge (identified in Table 1 by g).

Metal complex, D, was 2,8-dihydrodibenzo[e,h]azulen-2-yl)-N-(1,1-dimethylethyl)-dimethylsilanamidetitanium dimethyl, prepared by reaction of the dilithium salt of 1,8-dihydro-dibenzo[e,h]azulene with dimethyl dichlorosilane followed by reaction with titanium tetrakis (dimethylamide) and boron trichloride to convert to the dichloride metal salt. The corresponding dimethyl compound was prepared by exchange with methylmagnesium chloride. The resulting complex has the following structure:

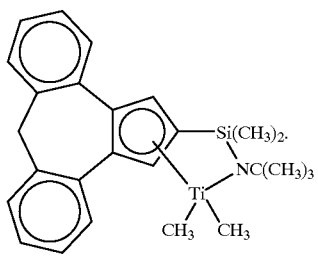

After polymerization for the indicated time period, the resulting solution was removed from the reactor into a nitrogen purged collection vessel containing 20 ml of a 10 weight percent toluene solution of hindered phenol antioxidant (Irganox™ 1010 from Ciba Geigy Corporation) and phosphorus stabilizer (Irgafos 168, also from Ciba-Geigy Corporation). Polymers formed are dried in a programmed vacuum oven with a maximum temperature of 145° C and an overnight heating cycle. Results are shown in Table 1.

bonded to Cp through a divalent bridging group, or Z is a divalent moiety lacking in delocalized π-electrons that is covalently bonded to Cp and M, or such a moiety comprising one σ-bond by which it is bonded to Cp, and a neutral two electron pair able to form a coordinate-covalent bond to M;

X is a monovalent anionic ligand group having up to 60 atoms other than hydrogen;

L independently each occurrence is a neutral ligating compound having up to 20 atoms;

X' is a divalent anionic ligand group having up to 60 atoms;

x is 0, 1, 2, or 3;

l is a number from 0 to 2, and x' is 0 or 1, (B) a cocatalyst able to form an active polymerization catalyst species in combination with (A); and (C) a conjugated diene having 4 or 5 carbons;

the molar ratio of (A):(B) being from 1:10,000 to 100:1 and the molar ratio of (C) to addition polymerizable compound being from 1:100,000 to 1:4.

TABLE 1

| Run | Catalyst (μmol) | Styrene g | Solvent (approx. g) | C₂H₄ (MPa) or (g) | comonomer (g) | Temp. °C. | H₂ kPa | Time minutes | Yield g | Efficiency Kg/g Ti | Tm °C. |
|---|---|---|---|---|---|---|---|---|---|---|---|
| 1 | A¹ (4) | 0 | IPE (858) | 3.5 MPa | BD (6.7) | 145 | 70 | 10 | 50.2 | 262 | 122 |
| 2* | A (4) | " | " | " | 0 | " | " | " | 24.0 | 126 | 135 |
| 3 | A (12) | " | " | 20 g | BD (6.3) | " | " | 47 | 18.1 | 332 | 102 |
| 4* | A (12) | " | " | " | 0 | " | " | 34 | 12.63 | 121 | 131 |
| 5* | B² (4) | " | " | " | BD (5.0) | " | " | 37 | 9.8 | 551 | 121 |
| 6* | B (2) | " | " | " | 0 | " | " | 12 | 12.8 | 134 | 134 |
| 7* | C³ (10) | " | " | " | BD (4.7) | " | " | 36 | 7.0 | 8 | 127 |
| 8* | C (2) | " | " | " | 0 | " | " | 12 | 16.9 | 93 | 134 |
| 9 | A (2.5) | 200 | TOL (675) | 2.0 MPa | BD (4.8) | 130 | 0 | 16 | 51.6 | 346 | 71 |
| 10* | A (5) | " | " | " | 0 | " | " | 16 | 50.5 | 172 | 65 |
| 11* | A (5) | " | " | " | PR (3.7) | " | " | 21.5 | 49.7 | 65 | 57 |
| 12 | D⁴ (2.5) | " | " | " | BD (5.5) | " | " | 16 | 98.1 | 820 | |
| 13* | D (2.5) | " | " | " | 0 | " | " | 16 | 74.4 | 622 | |
| 14 | E⁵ (2.5) | " | " | " | BD (5.1) | " | " | 16 | 127.6 | 1,066 | |
| 15* | E (2.5) | " | " | " | 0 | " | " | 16 | 52.8 | 441 | |

*comparative, not an example of the invention

[1] (1H-cyclopenta[l]phenanthrene-2-yl)dimethyl(t-butylamido)silanetitanium dimethyl, prepared according to the teachings of U.S. Pat No. 6,150,297.

[2] (t-butylamido)dimethylsilyl(η⁵-tetramethylcyclopentadienyl)titanium dimethyl.

[3] dimethylsilane bis(2-methyl-4-phenylinden-1-yl)zirconium 1,4-diphenyl-1,3-pentadiene, prepared according to the teachings of U.S. Pat. No. 5,972,822.

[4] (2,8-dihydrodibenzo[e,h]azulen-2-yl)-N-(1,1-dimethylethyl)dimethylsilanamide dimethyltitanium, prepared according to U.S. Ser. No. 09/879,463.

[5] (1H-cyclopenta[l]phenanthrene-2-yl)dimethyl(t-butylamido)silanetitanium dimethyl, prepared according the teachings of U.S. Pat. No. 6,150,297.

What is claimed is:

1. A process for the polymerization of addition polymerizable monomers, comprising contacting an olefin monomer or mixture of olefin monomers under addition polymerization conditions with a catalyst composition comprising the reaction product or admixture of:

(A) a metal complex corresponding to the formula:
CpZM$_x$L$_l$X'$_{x'}$, (IA);

where Cp is an anionic, polycyclic, fused ring ligand system containing at least 4 fused rings, and bonded to M by means of delocalized π-electrons;

M is titanium, zirconium or hafnium in the +2, +3 or +4 formal oxidation state;

Z is either a cyclic or noncyclic ligand group containing delocalized π-electrons, including a second polycyclic ring system group as herein previously disclosed for Cp, said Z being bonded to M by means of delocalized π-electrons and optionally covalently 2. The process according to claim 1 wherein the metal complex corresponds to the formula:

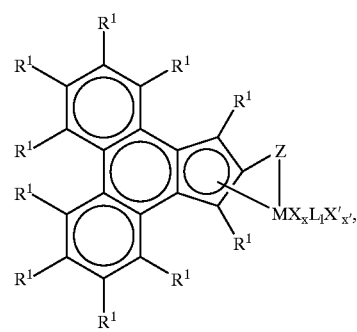

(IB)

-continued

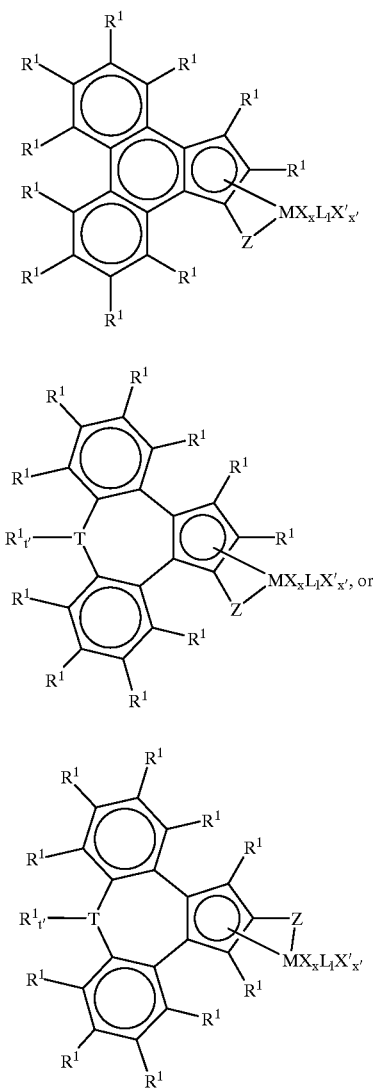

wherein,
T is carbon, or nitrogen;
when T is carbon, t' is 2, and when T is nitrogen, t' is 1;
M is titanium, zirconium or hafnium in the +2, +3 or +4 formal oxidation state;

$R^1$ independently each occurrence is hydrogen, hydrocarbyl, silyl, germyl, halide, hydrocarbyloxy, hydrocarbylsiloxy, hydrocarbylsilylamino, di(hydrocarbyl)amino, hydrocarbyleneamino, di(hydrocarbyl)phosphino, hydrocarbylenephosphino, hydrocarbylsulfido, halo-substituted hydrocarbyl, hydrocarbyloxy-substituted hydrocarbyl, silyl-substituted hydrocarbyl, hydrocarbylsiloxy-substituted hydrocarbyl, hydrocarbylsilylamino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylenephosphino-substituted hydrocarbyl, or hydrocarbylsulfido-substituted hydrocarbyl, said $R^1$ group having up to 40 atoms not counting hydrogen atoms, and optionally two or more of the foregoing adjacent $R^1$ groups may together form a divalent derivative thereby forming a saturated or unsaturated fused ring, and further optionally one or more of the carbons of any of the rings may be replaced by a nitrogen or sulfur atom;

Z is a divalent moiety lacking in delocalized π-electrons, or such a moiety comprising one σ-bond and a neutral two electron pair able to form a coordinate-covalent bond to M, said Z comprising boron, or a member of Group 14 of the Periodic Table of the Elements, and also comprising nitrogen, phosphorus, sulfur or oxygen;

X is a monovalent anionic ligand group having up to 60 atoms exclusive of the class of ligands that are cyclic ligand groups bound to M through delocalized π-electrons;

L independently each occurrence is a neutral ligating compound having up to 20 atoms;

X' is a divalent anionic ligand group having up to 60 atoms;

x is 0, 1, 2, or 3;
l is a number from 0 to 2, and
x' is 0 or 1.

3. The process according to claim 1 wherein the metal complex is:
(t-butylamido)dimethyl(1H-cyclopenta[1]-phenanthrene-2-yl)silanetitanium(IV) dimethyl.

4. The process of claim 1 wherein component (C) is 1,3-butadiene, 1,3-pentadiene, or 3-methyl-1,3-butadiene.

5. The process of claim 1 wherein ethylene and a vinylaromatic monomer are copolymerized.

6. The process of claim 1 wherein ethylene and styrene are copolymerized.

* * * * *